United States Patent
Jung et al.

(10) Patent No.: US 11,781,211 B2
(45) Date of Patent: Oct. 10, 2023

(54) METHOD FOR COATING ON SURFACE OF MEDICAL PEEK MATERIAL, TITANIUM HAVING MICROPOROUS STRUCTURE

(71) Applicant: OSONG MEDICAL INNOVATION FOUNDATION, Cheongju-si (KR)

(72) Inventors: Tae Gon Jung, Cheongju-si (KR); Yong Hoon Jeong, Cheongju-si (KR); Su Won Lee, Yangsan-si (KR); Kwang Min Park, Cheongju-si (KR); Jae Woong Yang, Sejong-si (KR); Jae Young Jung, Cheongju-si (KR); Kwan Su Kang, Cheongju-si (KR)

(73) Assignee: OSONG MEDICAL INNOVATION FOUNDATION, Chungju-si (KR)

( * ) Notice: Subject to any disclaimer, the term of this patent is extended or adjusted under 35 U.S.C. 154(b) by 472 days.

(21) Appl. No.: 16/642,364

(22) PCT Filed: Jul. 19, 2018

(86) PCT No.: PCT/KR2018/008158
§ 371 (c)(1),
(2) Date: Feb. 26, 2020

(87) PCT Pub. No.: WO2019/078455
PCT Pub. Date: Apr. 25, 2019

(65) Prior Publication Data
US 2021/0079532 A1    Mar. 18, 2021

(30) Foreign Application Priority Data
Oct. 19, 2017 (KR) .......... 10-2017-0135664

(51) Int. Cl.
*C23C 14/20* (2006.01)
*C23C 14/35* (2006.01)
(Continued)

(52) U.S. Cl.
CPC ........... *C23C 14/20* (2013.01); *B24B 31/102* (2013.01); *C23C 14/205* (2013.01); *C23C 14/35* (2013.01);
(Continued)

(58) Field of Classification Search
CPC ... C23C 14/20; C23C 14/205; C23C 14/5853; C23C 14/5873; C23C 14/588;
(Continued)

(56) References Cited

U.S. PATENT DOCUMENTS 8,449,347 B2 * 5/2013 Sutton ................... B24B 1/005
451/60
9,062,381 B2 * 6/2015 Wang ...................... A61L 27/04
(Continued)

FOREIGN PATENT DOCUMENTS

CN  105290950 A  2/2016
DE  202017103016 U1  8/2017
(Continued)

OTHER PUBLICATIONS

"Anodizing". www.wikipedia.org [https://en.wikipedia.org/wiki/Anodizing].*

(Continued)

*Primary Examiner* — Michael A Band
(74) *Attorney, Agent, or Firm* — LeePI

(57) ABSTRACT

In a method for coating on a surface of a medical PEEK material with titanium to have a microporous structure, titanium is coated on a surface of polyether ether ketone (PEEK) via magnetron sputtering. The surface of the titanium coated on the surface of PEEK is polished via an electromagnetic polishing apparatus. A thin-film with titanium dioxide ($TiO_2$) having a microporous structure is formed on the polished surface of the titanium via an anodic oxidation treatment.

8 Claims, 9 Drawing Sheets

(51) Int. Cl.
  *C23C 14/58* (2006.01)
  *C23C 28/00* (2006.01)
  *B24B 31/10* (2006.01)
  *C25D 11/26* (2006.01)
  *C25D 11/34* (2006.01)

(52) U.S. Cl.
  CPC ........ *C23C 14/588* (2013.01); *C23C 14/5853* (2013.01); *C23C 14/5886* (2013.01); *C23C 28/322* (2013.01); *C23C 28/3455* (2013.01); *C25D 11/26* (2013.01); *C25D 11/34* (2013.01)

(58) Field of Classification Search
  CPC ..... C23C 14/5886; C23C 14/14; C23C 14/35; C23C 14/3485; C23C 14/505; C25D 11/26; C25D 11/34; B24B 31/102; H01J 37/3467
  See application file for complete search history.

(56) References Cited

U.S. PATENT DOCUMENTS

| | | | |
|---|---|---|---|
| 9,136,096 B2* | 9/2015 | Godet | C23C 14/345 |
| 2004/0121290 A1* | 6/2004 | Minevski | A61L 31/086 |
| | | | 433/201.1 |
| 2013/0216711 A1* | 8/2013 | Fiedler | C23C 14/35 |
| | | | 427/255.28 |
| 2015/0075995 A1 | 3/2015 | Barker et al. | |
| 2016/0153081 A1 | 6/2016 | Lai et al. | |

FOREIGN PATENT DOCUMENTS

| | | |
|---|---|---|
| JP | H0852650 A | 2/1996 |
| JP | 3211656 U | 7/2017 |
| KR | 20-2000-0005310 A | 3/2002 |
| KR | 20030031664 A | 4/2003 |
| KR | 10-2003-0031664 A | 10/2003 |
| KR | 10-0993310 B1 | 11/2010 |
| KR | 10-1046674 B1 | 7/2011 |
| KR | 10-2012-0105280 A | 6/2013 |
| WO | 2010103815 A1 | 9/2010 |

OTHER PUBLICATIONS

Extended European search report dated Apr. 7, 2021.
International search report dated Oct. 26, 2018.

* cited by examiner

METHOD FOR COATING ON SURFACE OF MEDICAL PEEK MATERIAL, TITANIUM HAVING MICROPOROUS STRUCTURE

BACKGROUND

1. Field of Disclosure

The present disclosure of invention relates to a method for coating on surface of medical PEEK material, and more specifically the present disclosure of invention relates to a method for coating on surface of medical PEEK material, titanium having microporous structure, in which titanium dioxide ($TiO_2$) thin-film having a micro-porous structure is formed on a surface of a material like polyether ether ketone (PEEK) or carbon fiber reinforced PEEK (CFR-PEEK) which is used for a medical material implanted to a human body like interbody fusion cages or devices.

2. Description of Related Technology

Generally, polyether ether ketone (PEEK) or carbon fiber reinforced PEEK (CFR-PEEK) is widely used for a material for interbody fusion cages or devices.

PEEK material is a kind of hard polymer, and a surface of the PEEK material have less biocompatibility (the ability of a material to perform with an appropriate host response in a specific situation), and thus, the surface of the PEEK material is reformed with a conventional treating method such as a thermal spray method using titanium which has relatively high biocompatibility.

Korean Patent No. 10-0993310 discloses a titanium coating method and a titanium coating apparatus using the thermal spray method for enhancing the coating quality.

However, in the disclosed thermal spray method, a thickness of the coating is between about 60 μm and about 100 μm, and thus the thickness of the coating is relatively large and an adhesive force with a substrate is relatively small. Thus, when the material coated with the disclosed thermal spray method is implanted to the human body, the coating is easy to be peeled.

Related prior arts are Korean Patent No. 10-1274229 and Korean Patent No. 10-0993310.

SUMMARY

The present invention is developed to solve the above-mentioned problems of the related arts. The present invention provides a method for coating on surface of medical PEEK material, capable of enhancing biocompatibility via coating titanium on the surface of medical PEEK or CFR-PEEK material by a magnetron sputtering method and via forming a thin-film with titanium dioxide ($TiO_2$) having a microporous structure via an anodic oxidation method.

According to an example embodiment, in the method, titanium is coated on a surface of polyether ether ketone (PEEK) via magnetron sputtering. The surface of the titanium coated on the surface of PEEK is polished via an electromagnetic polishing apparatus. A thin-film with titanium dioxide ($TiO_2$) having a microporous structure is formed on the polished surface of the titanium via an anodic oxidation treatment.

In an example, in the coating titanium, a titanium target may be disposed inside of a chamber of a magnetron sputtering apparatus. An unalive gas may be injected into the chamber. A predetermined voltage may be applied to the titanium target with predetermined temperature and pressure conditions, to coat the titanium on the surface of PEEK.

In an example, in the coating titanium on the surface of PEEK, the pressure may be about $5 \times 10^{-3}$ torr, the temperature may be between about 100° C. and about 150° C., and the power may be between about 2 kW and about 3 kW.

In an example, a thickness coated on the surface of PEEK may be between about 2.5 μm and about 3.0 μm.

In an example, in the coating titanium on the surface of PEEK, a titanium plasma may be generated by the voltage applied between the titanium target and the PEEK with rotating the PEEK, and a magnetic field generated by an electrode reaches the PEEK, so that titanium plasma ions generated around a surface of the titanium target may be coated on the surface of PEEK.

In an example, the electromagnetic polishing apparatus may include a magnetic field generator, a magnetic field converter, a polishing receiver and a receiving plate. The magnetic field generator may have a permanent magnet generating an N pole magnetic field and a permanent generating an S pole magnetic field. The magnetic field converter may rotate the magnetic field generator, to covert the positions of the N pole magnetic field and the S pole magnetic field repeatedly by a relatively short period. The polishing receiver may be configured, into which the PEEK having the surface coated with titanium and a polishing material having magnetism are provided, into which the magnetic field generated by the magnetic field generator is supplied. The receiving plate may be disposed over the magnetic field converter and may receive the polishing receiver.

In an example, in the polishing, a liquid and a polishing material may be provided into a polishing receiver having a predetermined volume. The PEEK having the surface coated with titanium may be disposed and fixed into the polishing receiver. The magnetic force may be generated to the polishing receiver via a magnetic field generator. The polishing material may move along a predetermined direction with respect to the PEEK having the surface coated with titanium due to the generated magnetic force, so that the titanium coated on the surface of the PEEK may be polished to be planarized In an example, the polishing material may be SUS 304.

In an example, in forming the thin-film with titanium dioxide, the PEEK coated with the polished titanium and platinum (Pt) may be dipped into an electrolyte of an anodic oxidation apparatus. An anode of a direct current power may be electrically connected to the PEEK coated with the polished titanium, and a cathode thereof may be electrically connected to platinum. In an example, a predetermined voltage and a predetermined current may be applied to the anode and the cathode in a predetermined temperature for the anodic oxidation of the surface of the polished titanium, so that the thin-film with titanium dioxide having the microporous structure may be formed.

In an example, the electrolyte may include 3.75 mole NaOH.

In an example, in forming the thin-film with titanium dioxide, the temperature may be about 18° C., the voltage may be between about 10V and about 15V, and the current may be between about 0.5 A and about 1 A.

According to the present example embodiments, a titanium thin-film having a thickness between about 1 μm and 3 μm is formed via a magnetron sputtering method which is one of physical vapor deposition methods, and thus the coating is more uniform and is more adhesive compared to the conventional coating method.

In addition, a thin-film with titanium dioxide TiO2 having a micro size porosity is formed on the surface of titanium coated on the surface of PEEK using the anodic oxidation method (anodization), so that biocompatibility with marrow may be enhanced.

In addition, an after treatment is performed on the coated titanium layer, and then uniform density of current is applied in the anodic oxidation method, and thus the porosity is uniformly formed. In addition, in the anodic oxidation method, instead of using the conventional acid electrolyte, a protocol using an alkali electrolyte is applied, and thus a danger due to the acid residue may be minimized.

In addition, in the coating titanium on the surface of PEEK, the optimized conditions such as the pressure of about $5\times10^{-3}$ torr, the temperature between about 100° C. and about 150° C. and the power between about 2 kW and about 3 kW, are applied, and thus the adhesion between two dissimilar substances may be increased.

In addition, the surface of titanium coated on PEEK is after-treated using the electromagnetic polishing apparatus, and thus in the anodic oxidation method, the uniform density of current is applied such that the anodic oxidation products may be more uniform.

REFERENCE NUMERALS

Figure 1A:
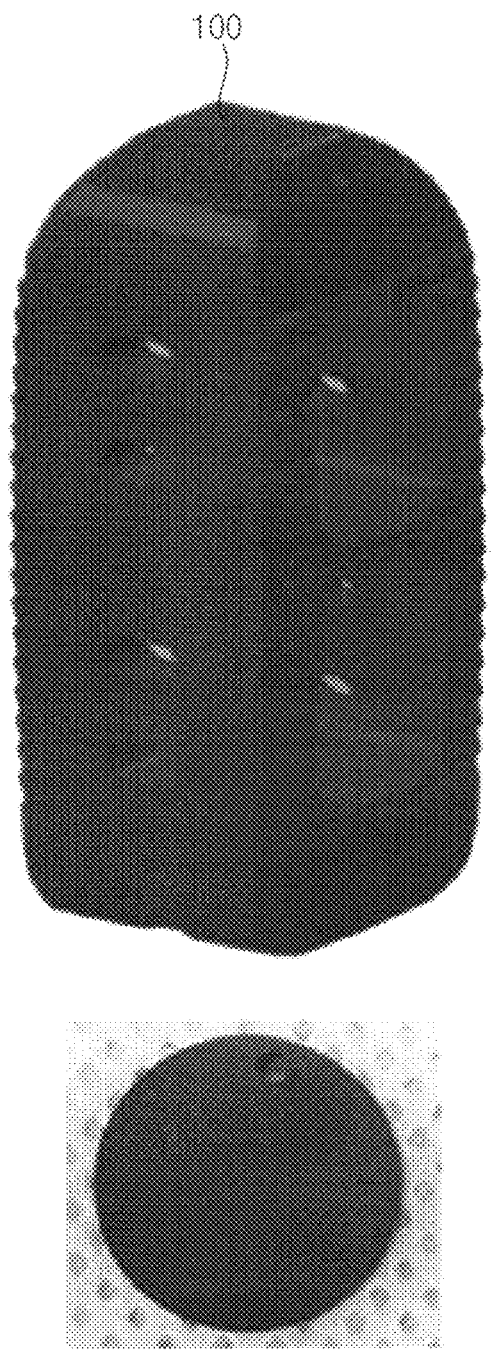
FIG. 1A, FIG. 1B and FIG. 1C are images showing states of PEEK respectively before the coating, after the sputtering and after the anodic oxidation.

10: magnetron sputtering apparatus 20: electromagnetic polishing apparatus
30: anodic oxidation apparatus

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

Figure 1B:
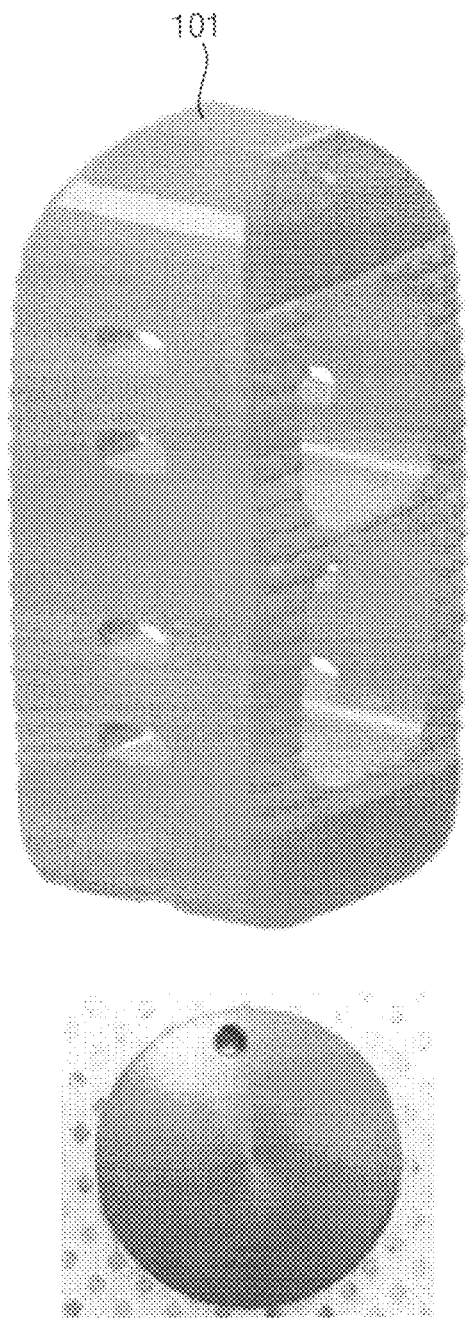
Figure 1C:
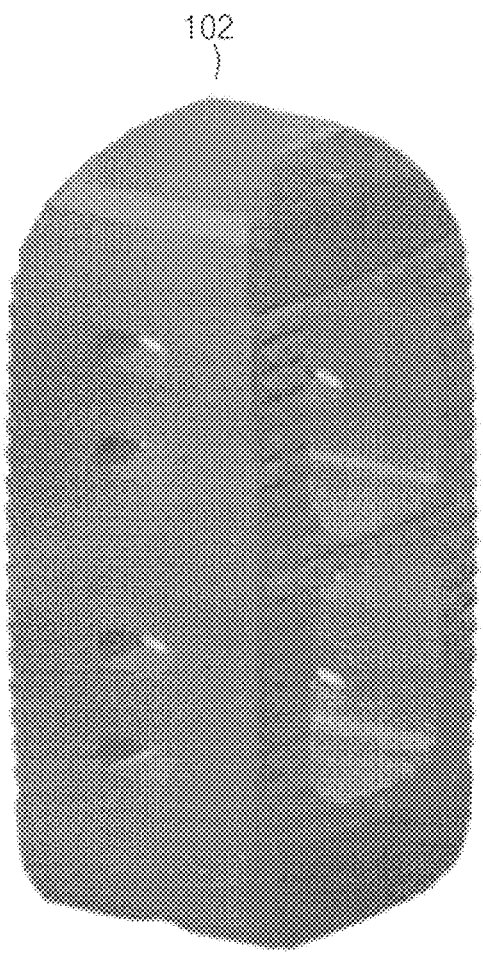
Figure 1C:
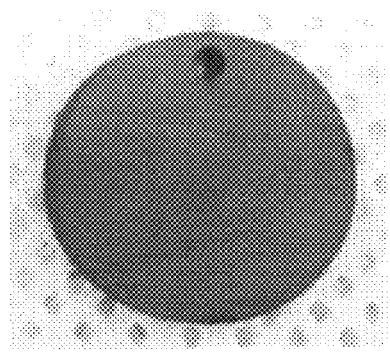
Figure 2:
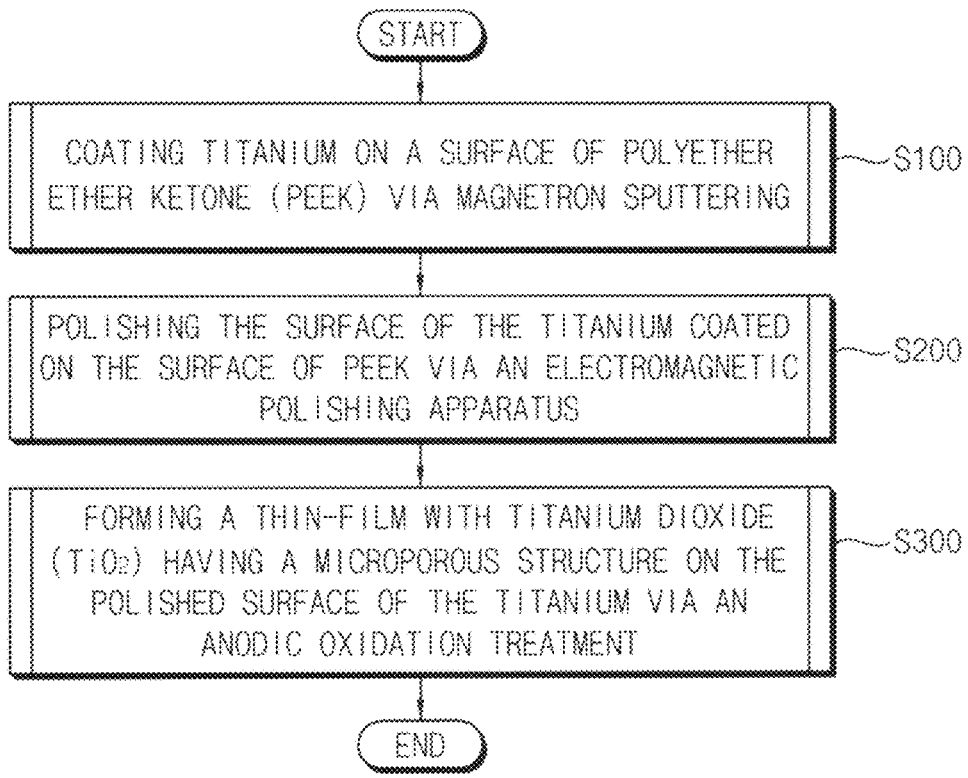
FIG. 2 is a flow chart showing a method for coating on a surface of a medical PEEK material according to an example embodiment of the present invention.

FIG. 1A, FIG. 1B and FIG. 1C are images showing states of PEEK respectively before the coating, after the sputtering and after the anodic oxidation. FIG. 2 is a flow chart showing a method for coating on a surface of a medical PEEK material according to an example embodiment of the present invention.

Referring to FIG. 1A and FIG. 2, in the method for coating titanium having a microporous structure, on a surface of a medical PEEK material, titanium is coated (deposited) on a surface of a polyether ether ketone (PEEK) via magnetron sputtering (step S100).

Here, a magnetron sputtering apparatus 10 is used for the coating, and a titanium (Ti) is targeted. Thus, the titanium is coated or deposited on the surface of the PEEK by the magnetron sputtering.

In the present example embodiment, the magnetron sputtering apparatus used for the coating is not limited as illustrated in the figure.

Figure 3:
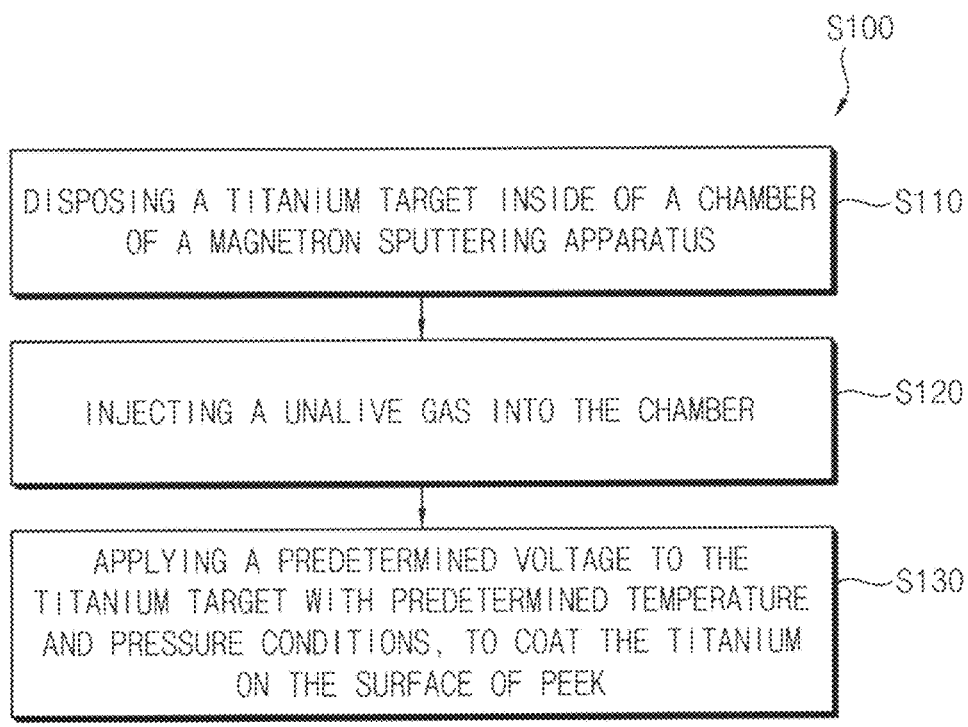
FIG. 3 is a flow chart showing a method for coating titanium, in the method for coating on the surface of the medical PEEK material in FIG. 2.
Figure 4:
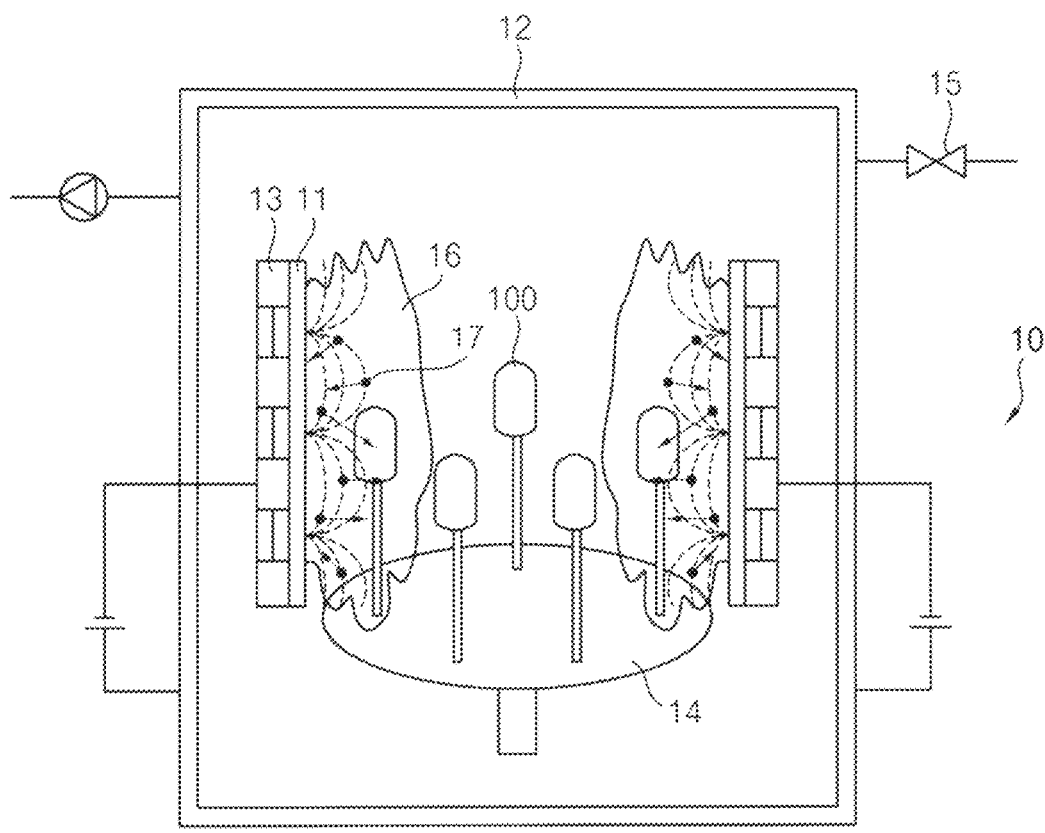
FIG. 4 is a schematic view illustrating a magnetron sputtering apparatus used in the method for coating titanium in FIG. 3.

FIG. 3 is a flow chart showing a method for coating titanium, in the method for coating on the surface of the medical PEEK material in FIG. 2. FIG. 4 is a schematic view illustrating a magnetron sputtering apparatus used in the method for coating titanium in FIG. 3.

Referring to FIGS. 3 and 4, the magnetron sputtering apparatus includes a chamber 12, an electrode 13, a substrate 14 and a gas providing unit 15. The chamber 12 forms a space for the sputtering inside of the chamber 12. A titanium target 11 is mounted on the electrode 13. A plurality of the PEEKs 100 is disposed on the substrate 14, and is disposed with each other by a predetermined distance. The gas providing unit 15 provides an unalive gas into the chamber 12.

As illustrated in FIG. 4, the titanium target 11 is mounted on the electrode 13 which is disposed inside of the chamber 12, and the plurality of the PEEKs 100 is positioned on the substrate 14, by a predetermined distance (step S110).

Then, the gas providing unit 15 injects the unalive gas like Argon (Ar) into the chamber 12 (step S120). Then, a predetermined voltage is applied to the titanium target 11 with predetermined temperature and pressure conditions, to coat or deposit titanium on the PEEK 100 (step S130).

For example, with rotating the PEEK 100, a titanium plasma 16 is generated by the voltage applied between the titanium target 11 and the PEEK 100, and a magnetic field generated by the electrode 13 reaches the PEEK 100, so that titanium plasma ions 17 generated around a surface of the titanium target 11 are coated or deposited on the PEEK 100.

Here, in the present example embodiment, the pressure may be about $5\times10^{-3}$ torr, the temperature may be between about 100° C. and about 150° C., and the power may be between about 2 kW and about 3 kW.

Thus, as illustrated in FIG. 1B, the PEEK 101 having the surface coated or deposited with titanium is formed, and here, the thickness of the coated or deposited titanium is between about 2.5 μm and about 3.0 μm.

Then, the surface of the PEEK 101 on which the titanium is coated or deposited is polished (after-treated) by an electromagnetic polishing apparatus 20 (step S200).

Figure 5:
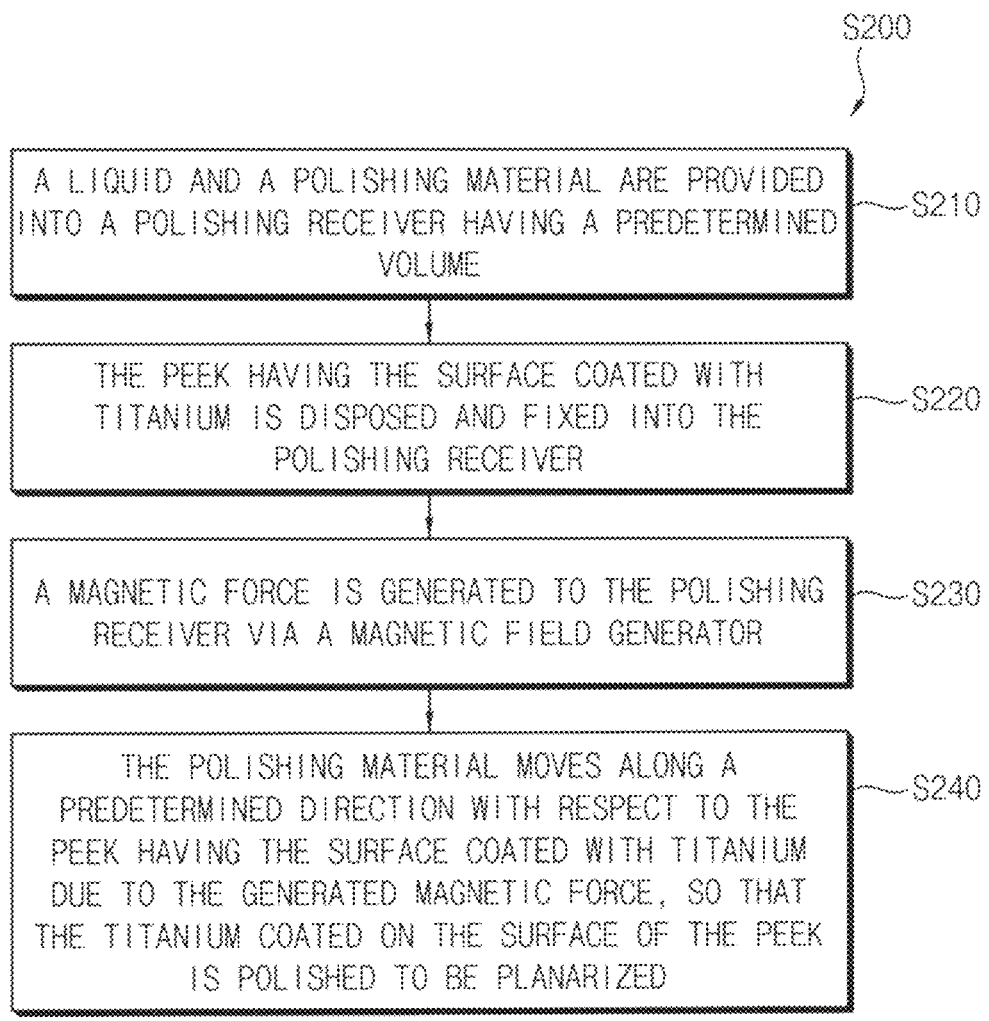
FIG. 5 is a flow chart showing a method for polishing using an electromagnetic polishing apparatus, in the method in FIG. 2.
Figure 6:
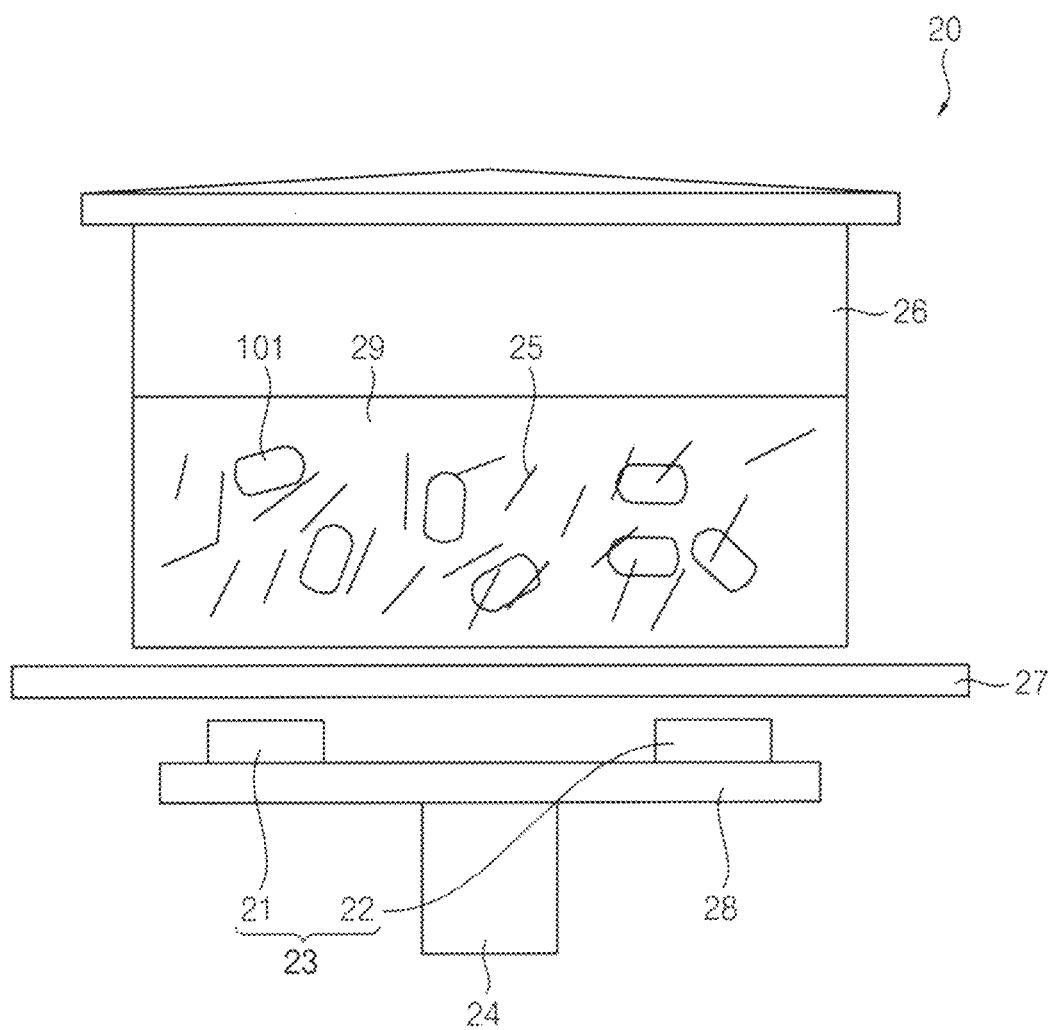
FIG. 6 is a schematic view illustrating the electromagnetic polishing apparatus used in the method for polishing in FIG. 5.

FIG. 5 is a flow chart showing a method for polishing using an electromagnetic polishing apparatus, in the method in FIG. 2. FIG. 6 is a schematic view illustrating the electromagnetic polishing apparatus used in the method for polishing in FIG. 5.

As illustrated in FIG. 6, the electromagnetic polishing apparatus 20 includes a magnetic field generator 23, a magnetic field converter 24, a polishing receiver 26 and a receiving plate 27. The magnetic field generator 23 has a permanent magnet 21 generating an N pole magnetic field and a permanent 22 generating an S pole magnetic field. The magnetic field converter rotates the magnetic field generator 23, to covert the positions of the N pole magnetic field and the S pole magnetic field repeatedly by a relatively short period. The PEEK 101 having the surface coated or deposited with titanium and a polishing material 25 having magnetism are provided into the polishing receiver 26, and the magnetic field generated by the magnetic field generator 23 is supplied into the polishing receiver 26. The receiving plate 27 is disposed over the magnetic field converter 24 and receives the polishing receiver 26.

Referring to FIGS. 5 and 6, a liquid 29 and the polishing material 25 are provided into the polishing receiver 26, and are mixed with each other in the polishing receiver 26 (step S210). Here, the polishing material 25 may be SUS 304.

Then, the PEEK on which the titanium is coated or deposited is provided into the polishing receiver 26 and is fixed inside of the polishing receiver 26 (step S220), and then a magnetic force is applied to the polishing receiver 26 via the magnetic field generator 23 (step S230).

Here, in the magnetic field generator 23, the permanent magnets 21 and 22 are fixed on a circular plate 28. The magnetic field generator 23 is disposed under the polishing receiver 26 and provides the magnetic force or the magnetic field into the polishing receiver 26. In the illustrated structure in FIG. 6, the circular plate 28 may be a nonmagnetic material blocking the magnetic force or the magnetic field. Alternatively, the magnetic field generator 23 may be an electromagnet.

Then, using the magnetic force applied to the polishing receiver 26, the polishing material 25 moves along a predetermined direction with respect to the PEEK having the surface coated or deposited with titanium, so that the titanium coated or deposited on the surface of the PEEK is polished to be planarized (step S240).

Here, the coated or deposited titanium moves with respect to the polishing material 25, and thus a relative friction force generated between the coated or deposited titanium and the polishing material 25 forces to polish the titanium on the surface of the PEEK.

Then, after polishing the surface of the titanium coated or deposited on the surface of the PEEK 101, a thin-film with titanium dioxide ($TiO_2$) having a microporous structure on the surface of the PEEK 101 is formed via an anodic oxidation apparatus (step S300).

Figure 7:
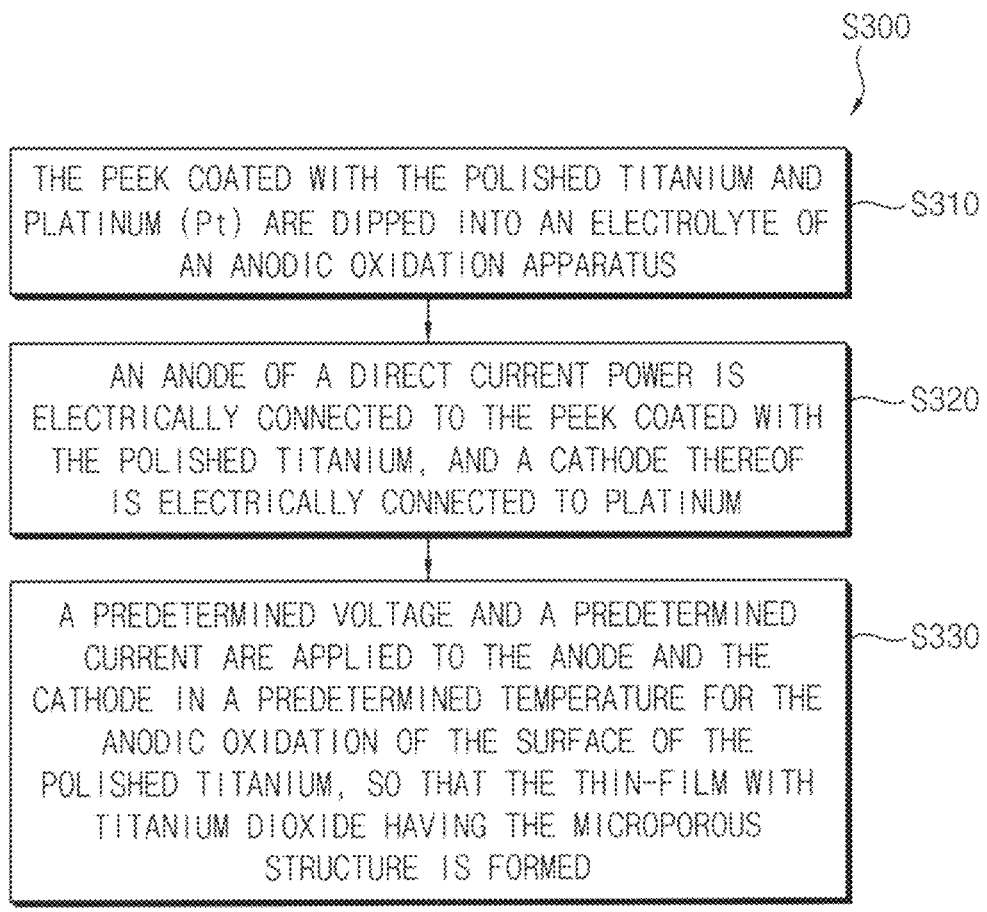
FIG. 7 is a flow chart showing a method for forming a thin-film with titanium dioxide ($TiO_2$), in the method in FIG. 2.
Figure 8:
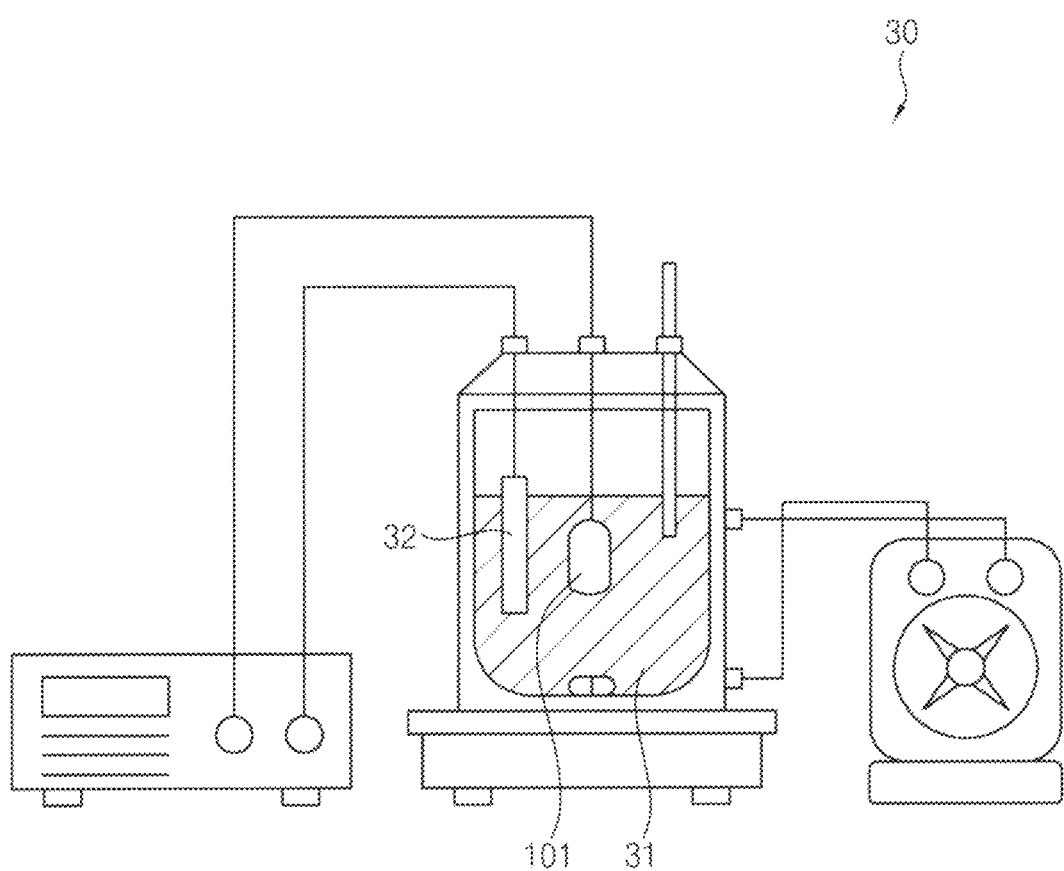
FIG. 8 is a schematic view illustrating an anodic oxidation apparatus used in the method for forming the thin-film in FIG. 7.

FIG. 7 is a flow chart showing a method for forming a thin-film with titanium dioxide ($TiO_2$), in the method in FIG. 2. FIG. 8 is a schematic view illustrating an anodic oxidation apparatus used in the method for forming the thin-film in FIG. 7.

Referring to FIGS. 7 and 8, the PEEK 101 and platinum (Pt) 32 are dipped into an electrolyte 31 of the anodic oxidation apparatus 30 (step S310).

Here, in the present example embodiment, the electrolyte 31 may include 3.75 mole NaOH.

Then, an anode of a direct current power is electrically connected to the PEEK 101, and a cathode of the direct current power is electrically connected to platinum 32 (step S320).

Then, a predetermined voltage and a predetermined current are applied to the anode and the cathode in a predetermined temperature for the anodic oxidation of the surface of the polished titanium, so that the thin-film with titanium dioxide having the microporous structure is formed (step S330). Here, in the present example embodiment, the temperature may be about 18° C., the voltage may be between about 10V and about 15V, and the current may be between about 0.5 A and about 1 A.

Thus, as illustrated in FIG. 1C, the PEEK 102 on which a titanium dioxide thin-film having the microporous structure (or a micro porosity) is formed, is completed.

According to the present example embodiments, a titanium thin-film having a thickness between about 1 μm and 3 μm is formed via a magnetron sputtering method which is one of physical vapor deposition methods, and thus the coating is more uniform and is more adhesive compared to the conventional coating method.

In addition, a thin-film with titanium dioxide TiO2 having a micro size porosity is formed on the surface of titanium coated on the surface of PEEK using the anodic oxidation method (anodization), so that biocompatibility with marrow may be enhanced.

In addition, an after treatment is performed on the coated titanium layer, and then uniform density of current is applied in the anodic oxidation method, and thus the porosity is uniformly formed. In addition, in the anodic oxidation method, instead of using the conventional acid electrolyte, a protocol using an alkali electrolyte is applied, and thus a danger due to the acid residue may be minimized.

In addition, in the coating titanium on the surface of PEEK, the optimized conditions such as the pressure of about $5\times10^{-3}$ torr, the temperature between about 100° C. and about 150° C. and the power between about 2 kW and about 3 kW, are applied, and thus the adhesion between two dissimilar substances may be increased.

In addition, the surface of titanium coated on PEEK is after-treated using the electromagnetic polishing apparatus, and thus in the anodic oxidation method, the uniform density of current is applied such that the anodic oxidation products may be more uniform.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A method for coating with titanium, comprising:
    coating titanium on a polyether ether ketone (PEEK) via magnetron sputtering;
    polishing the titanium coated on the PEEK via an electromagnetic polishing apparatus; and
    forming a thin-film with titanium dioxide ($TiO_2$) having a microporous structure on a polished surface of the titanium via an anodic oxidation treatment,
    wherein in the coating titanium on the PEEK,
        a titanium target is mounted on an electrode,
        a plurality of PEEKs disposed on a substrate and each of the PEEKs is spaced from each other by a predetermined distance,
        each of the PEEKs is independently rotated on the substrate and a titanium plasma is generated by a predetermined voltage applied between the titanium target and the PEEKs while rotating the PEEKs, and a magnetic field generated by the electrode reaches the PEEKs, so that titanium plasma ions generated around a surface of the titanium target are coated on each of the PEEKs via the magnetron sputtering,
    wherein in the polishing,
        a liquid and a polishing material are provided into a polishing receiver having a predetermined volume; and
        the PEEKs, each having a surface coated with the titanium via the magnetron sputtering, are disposed and fixed into the polishing receiver, with the PEEKs completely immersed in the liquid,
    wherein the electromagnetic polishing apparatus comprises:
        a magnetic field generator having a permanent magnet generating an N pole magnetic field and a permanent generating an S pole magnetic field;
        a magnetic field converter rotating the magnetic field generator, to rotate positions of the N pole magnetic field and the S pole magnetic field, wherein the positions of the N pole magnetic field and the S pole magnetic field are repeatedly rotated;
        the polishing receiver configured into which the PEEKs each having the surface coated with titanium and the polishing material having magnetism are provided, into which the magnetic field generated by the magnetic field generator is supplied; and
        a receiving plate disposed over the magnetic field converter and receiving the polishing receiver,
    wherein in the polishing, after completely immersing the PEEKs in the liquid,
        a magnetic force is generated to the polishing receiver via the magnetic field generator; and
        the polishing material moves along a predetermined direction with respect to each of the PEEKs due to the magnetic force, so that the titanium coated on each of the PEEKs is polished to be planarized.

2. The method of claim 1, wherein in the coating titanium,
    disposing a titanium target inside of a chamber of a magnetron sputtering apparatus; injecting Argon (Ar) gas into the chamber; and
    applying the voltage to the titanium target with predetermined temperature and pressure conditions, to coat the titanium on the PEEKs.

3. The method of claim 2, wherein in the coating titanium on the PEEKs,
    the predetermined pressure is about $5\times10^{-3}$ torr, the predetermined temperature is between about 100° C. and about 150° C., and the predetermined power is between about 2 kW and about 3 kW.

4. The method of claim 1, wherein a thickness of the titanium on each of the PEEKs is between about 2.5 µm and about 3.0 µm.

5. The method of claim 1, wherein the polishing material is SUS 304.

6. The method of claim 1, wherein in forming the thin-film with titanium dioxide,
    a platinum (Pt) and the PEEKs with the polished surface of the titanium are dipped into an electrolyte of an anodic oxidation apparatus;
    an anode of a direct current power is electrically connected to the PEEKs, and a cathode thereof is electrically connected to the platinum (Pt); and
    a predetermined voltage and a predetermined current are applied to the anode and the cathode in a predetermined temperature for an anodic oxidation of the polished surface of the titanium, so that the thin-film with titanium dioxide having the microporous structure is formed.

7. The method of claim 6, wherein the electrolyte comprises 3.75 mole NaOH.

8. The method of claim 6, wherein in forming the thin-film with titanium dioxide,
    the predetermined temperature is about 18° C., the predetermined voltage is between about 10V and about 15V, and the predetermined current is between about 0.5 A and about 1 A.

* * * * *